United States Patent [19]

Warren

[11] 4,435,384

[45] Mar. 6, 1984

[54] TRANSFER FACTOR COMPOSITION AND SKIN TREATMENT

[75] Inventor: Stanley L. Warren, Hallendale, Fla.

[73] Assignee: Viragen, Inc., Hasbrouck Heights, N.J.

[21] Appl. No.: 373,816

[22] Filed: Apr. 30, 1982

[51] Int. Cl.³ .................. A61K 35/14; A61K 39/00
[52] U.S. Cl. ................................ 424/101; 424/88; 424/89
[58] Field of Search .............. 424/95, 88, 89, 101

[56] References Cited

PUBLICATIONS

Cumulated Index Medicus–1979, p. 11346.
Cumulated Index Medicus–1978, p. 10942.

*Primary Examiner*—Sam Rosen
*Attorney, Agent, or Firm*—Blum Kaplan

[57] ABSTRACT

A topical composition including transfer factor for dermatological treatment is provided. The composition may be used for cosmetic purposes and for treatment of skin lesions, such as blemishes, acne, herpes simplex, condyloma and the like. The treatment includes application of the topical composition to the infected sites.

17 Claims, No Drawings

TRANSFER FACTOR COMPOSITION AND SKIN TREATMENT

BACKGROUND OF THE INVENTION

This invention relates generally to a topical composition, and more particularly to a topical composition including transfer factor and a method of skin treatment.

Herpes simplex virus type 1 causes mucocutaneous lesions around the mouth. The type 2 virus, which has been shown to be venereal transmitted, causes lesions in the genital area. Various treatments have been proposed and the viruses have resisted the various treatments. Recent proposals include the use of various synthetic acyclic purine nucleosides as in U.S. Pat. No. 4,199,574. Another proposal appears in Kahn, A. et al.: Transfer Factor in the Treatment of Herpes Simplex Types 1 and 2, Dermatologica 163: 177–185 (1981) which suggests that injections of transfer factor may be helpful in controlling recurrent herpes simplex. Notwithstanding these reported improvements, it is desirable to treat the infections by applying topical composition.

Treatment of herpes simplex, condyloma, acne and other skin lesions by way of application of a topical composition in the form of a cream or ointment is preferred to parenteral administration as a topical composition may be applied conveniently without the necessity of a physician visit. Additionally, topical application permits application of the active ingredient directly to the lesion and the surrounding area as required. Significantly, application of a topical composition avoids parenteral injection, thus minimizing foreign protein exposure to the patient. Accordingly, it would be desirable to provide an improved topical composition effective in the treatment of skin lesions, such as skin blemishes, herpes simplex condyloma and the like.

SUMMARY OF THE INVENTION

Generally speaking, in accordance with the invention, a topical composition including transfer factor for dermatological use is provided. The topical composition in accordance with the invention includes a non-toxic vehicle and transfer factor and may include an enhancing penetrant dispersed therein. A typical composition in accordance with the invention includes between about 1 to 10 Units of transfer factor per gram of total composition and may contain between 0 to 15 percent by weight of a penetrant, such as dimethyl sulfoxide (DMSO) or low molecular weight dextran. The skin lesions are treated by applying the topical composition to the infected area between three and five applications per day. A 30 gram sample is sufficient for about 21 days of treatment.

Accordingly, it is an object of the invention to provide an improved topical composition for dermatological use.

Another object of the invention is to provide an improved composition including transfer factor.

A further object of the invention is to provide an improved topical composition containing transfer factor for cosmetic application to the skin.

Yet another object of the invention is to provide an improved topical composition for treatment of skin lesions such as blemishes, herpex simplex and condylomata.

Yet a further object of the invention is to provide an improved topical composition for skin treatment containing transfer factor and an enhancing penetrant.

Still another object of the invention is to provide a new method of skin treatment.

Still a further object of the invention is to provide an improved method of skin treatment by applying a topical composition including transfer factor.

Another object of the invention is to provide an improved method of treating herpes simplex by applying a topical composition including transfer factor and an enhancing penetrant to the infected region.

Still other objects and advantages of the invention will in part be obvious and will in part be apparent from the specification.

The invention accordingly comprises the several steps and the relation of one or more of such steps with respect to each of the others, and the composition possessing the features, properties, and the relation of constituents, which are exemplified in the following detailed disclosure, and the scope of the invention will be indicated in the claims.

DESCRIPTION OF THE PREFERRED EMBODIMENTS

The topical composition prepared in accordance with the invention includes transfer factor in a gentle vehicle. The vehicle is preferably a gentle, non-toxic carrier and may be an unscented moisturizing formula generally used for dry skin care. The preferred composition includes an enhancing penetrant, such as dimethyl sulfoxide or low molecular weight dextran for increasing penetration of the transfer factor into the skin.

Transfer factor is obtained from the lymphocytes of a donor having no history of recurrent infection by herpes virus. It is believed to be a low molecular weight (5,000–10,000) dialysable protein made up of amino acids with a possible RNA base. The transfer factor may be prepared as documented in the medical literature. For example, detailed preparation of transfer factor is described in Warren, S.: Transfer Factor for the Practicing Allergist-Immunologist, Annals of Allergy, 39:130–132 (August, 1977). The procedure I described therein for production of crude transfer factor is set forth as follows for convenience.

1. Obtain a heparinized whole blood sample from a suitable donor. About 48 ml is required (4 green top vacutainers).

2. Transfer the well mixed blood to a clear 50 ml cylinder. Cover and allow to stand at room temperature to settle for about two hours.

3. Prepare a clear 50 ml syringe by removing the plunger and loosely stuffing the barrel with clear cotton wool and sealing the needle outlet with a cover.

4. Carefully, using a transfer pipet, transfer the plasma and buffy coat layer from the cylinder into the prepared syringe so that the plasma is soaked up by the cotton wool and no free liquid is in the syringe.

5. Carefully replace the plunger into the syringe barrel without compressing any of the plasma saturated cotton wool. Incubate the syringe and contents for 20 minutes at 37° C.

6. Open the needle outlet and compress the cotton wool so as to express the lymphocyte-rich plasma completely into a clear centrifuge tube. Discard the cotton wool.

7. Remove a small quantity of this cell suspension for determining the absolute cell count. (The total cell count of the suspension).

8. Gently centrifuge the cell suspension for 15 minutes and then decant the plasma without disturbing the cell button at the bottom of the centrifuge tube.

9. Wash the cells three times with about 25 ml of 0.5N saline. Each time disperse the cells in the wash fluid thoroughly, centrifuge and discard the wash solution.

10. Reconstitute the cell suspension by adding sufficient normal saline so that 1 ml of the final solution will contain $10^8$ cells as a concentration. ($10^8$ cells/ml).

11. Stopper the tube and alternately freeze and thaw the suspension a total of five times.

12. After the final thaw centrifuge the disrupted cell suspension at 2500 RPM for 15 minutes.

13. Decant the supernatant fluid into a syringe fitted with a sterile millipore filter.

14. Express the fluid through the millipore filter into sterile vials or aliquots using aseptic technique.

15. Retain one aliquot for sterility testing and potency testing, and store the balance in the freezer for later use. This final solution represents crude transfer factor extract.

The final solution prepared in the above manner contains approximately 1 Unit of transfer factor per milliliter of solution. (Defined as 1 Unit = $10^8$ cells.)

The transfer factor topical composition is prepared by mixing the transfer factor in a vehicle so that the transfer factor is present in a concentration of about 1 Unit per gram of composition. The preferred composition may also include up to about 15 weight percent of an enhancing penetrant, such as DMSO or low molecular weight dextran. It is most preferred that about 5% by weight of DMSO be used as human tests indicate that there is no effect from the DMSO at this concentration as it penetrates. A low molecular weight dextran of about 4,000 daltons can be substituted for the DMSO. When the dextran is utilized, the same percent by weight is preferably included.

During treatment with the transfer factor, the composition is applied to the infected area about four times per day. A 30 gram sample is sufficient for about 21 days of treatment. Thus, a patient applies about 30 Units of transfer factor over a 21 day period.

The vehicle utilized in preparing the composition is not critical. The vehicle may be any cosmetically acceptable vehicle which does not denature the transfer factor and which is non-toxic. It has been found that unscented moisturizing formulas generally utilized for dry skin care are suitable. Such moisturizing formulas generally are water and oil emulsions in which the transfer factor can be dispersed. Preferably, the vehicle is a lyophile non-toxic base. One such vehicle utilized in the following case studies is a Eucerin moisturizing formula obtained from Beiersdorf, Inc. of South Norwalk, Conn. The Eucerin moisturizing formula is a water in oil emulsion and is identified as containing water, petrolatum, mineral oil, mineral wax, wool wax alcohol and 2-bromo-2-nitropropane 1,3 diol.

The following case studies demonstrate the positive results obtained by utilizing the transfer factor composition prepared in accordance with the invention. The transfer factor utilized was prepared by utilizing scale-up techniques of the procedure outlined above which permit purification of large numbers of lymphocytes which are purified by common extraction utilizing the adherence of granulocytes to glass wool fibers. This permits harvesting from a mixed leukocyte preparation of 90% plus purified lymphocytes. The lymphocytes were then analyzed as to quantity and their cytoplasmic contents were obtained by destroying the cell walls using ultrasonic techniques. The transfer factor was then obtained from the cytoplasmic extraction, concentrated and passed through a molecular sieve which harvested only those fractions of molecular weight which include the transfer factor.

The following case studies utilized transfer factor prepared in accordance with this procedure dispersed in a Eucerin base with 5% DMSO added. Each of these case studies covered a period of about three months. They are set forth as illustrative and not in a limiting sense.

Case 1

Female patient A had herpes simplex outbreaks for about three years in the vagina and vulva on a monthly basis preceeding menstruation. The ointment was applied to the infected area on the basis of four times per day. Within 24 hours all pain and irritation had ceased. Within 48 hours significant healing of the lesions was observed. By 72 hours all lesions had cleared. No recurrence to date.

Case 2

Female patient B had weekly buccal herpes simplex lesions for over four years. The patient applied the ointment to the infected sites on the basis of four times per day. Within 24 hours all local irritation symptoms were abolished. Within 48 hours the lesions had disappeared. There have been no recurrent problems to date.

Case 3

Male patient C had multiple condylomatous growth about the neck area for several years which required periodic removal by hyfrication for control. The patient applied the ointment to the condylomata on the basis of four times per day. Within 24 hours all discomfort and irritation was significantly reduced. Within four days most of the condylomatous growth had disappeared. By the end of two weeks all the condylomatous growth had disappeared. No recurrence has been experienced to date.

Case 4

Male patient E had multiple condylomata on the fingers of both hands for at least two years. The patient applied the ointment on the basis of four times per day to the affected areas. At 48 hours there was a visible diminution in the size of the lesions. All lesions were cleared by the end of 14 days. There has been no recurrence of the lesions to date.

Case 5

Female patient E had a herpes simplex infection of the vulva and vagina for a period of over five years with outbreaks occurring every two to three months. The patient applied the ointment to the lesions and surrounding areas at least four times per day. All pain and irritation were greatly reduced within the first 24 hours. Within 48 hours major healing had occurred. No recurrence problems have been reported to date.

Case 6

Female patient F reported recurrent outbreaks of buccal herpes simplex for about two years. The ointment was applied to the lesions on the basis of four times per day. Discomfort and pain disappeared within 24 hours. By 48 hours significant healing of the lesions was observed. At the end of 96 hours all lesions were cleared. No recurrence has been observed to date.

It will thus be seen that the objects set forth above, among those made apparent from the preceding description, are efficiently attained and, since certain changes may be made in carrying out the above method and in the composition set forth without departing from the spirit and scope of the invention, it is intended that all matter contained in the above description shall be interpreted as illustrative and not in a limiting sense.

It is also understood that the following claims are intended to cover all of the generic and specific features of the invention which, as a matter of language, might be said to fall therebetween.

Particularly it is to be understood that in said claims, ingredients or compounds recited in the singular are intended to include compatible mixtures of such ingredients wherever the sense permits.

What is claimed is:

1. A topical composition for dermatological treatment comprising an ointment-type vehicle and an effective amount of transfer factor dispersed therein.
2. The topical composition of claim 1, further including an effective amount of an enhancing penetrant.
3. The topical composition of claim 1, wherein the vehicle is a non-toxic lyophilic base.
4. The topical composition of claim 1, wherein the transfer factor is present in the amount of up to about 10 Units ($10^8$ cells per Unit) per gram of composition.
5. The topical composition of claim 4, further including an effective amount of an enhancing penetrant.
6. The topical composition of claim 5, wherein the penetrant is selected from the group consisting of dimethyl sulfoxide, low molecular weight dextran, and mixtures thereof.
7. The topical composition of claim 6, wherein the penetrant is present up to about 15 percent by weight, based on the total weight of the composition.
8. The topical composition of claim 7, wherein the penetrant is dimethyl sulfoxide.
9. The topical composition of claim 7, wherein the penetrant is a low molecular weight dextran.
10. A topical composition for the treatment of herpes simplex comprising a non-toxic lyophile base between about 1 and 10 Units ($10^8$ cells per Unit) per gram of composition and about 1 and 15 percent by weight of dimethyl sulfoxide.
11. A method of dermatological treatment comprising applying to the affected skin a topical composition comprising a vehicle including transfer factor dispersed therein.
12. The method of claim 8, wherein the composition is applied to the skin between three and four times per day.
13. The method of claim 11, wherein the composition includes about 1 Unit of transfer factor per gram of composition.
14. A method of treating herpes simplex comprising applying to the infected region of the skin a composition including a herpes simplex effective amount of transfer factor.
15. A method of treating condyloma comprising applying to the infected region of the skin a topical composition including a condyloma effective amount of transfer factor.
16. A method of treating acne comprising applying to the infected region of the skin a topical composition including an acne effective amount of transfer factor.
17. A topical cosmetic composition comprising a non-toxic lyophilic base and an effective amount of transfer factor dispersed therein.

* * * * *